(12) United States Patent
Baiker et al.

(10) Patent No.: US 6,376,713 B1
(45) Date of Patent: Apr. 23, 2002

(54) PROCESS FOR THE PREPARATION OF AMINES

(75) Inventors: Alfons Baiker, Opfikon (CH); Achim Fischer, Gelnhausen (DE); Tamas Mallat, Zürich; Oleg Werbitzky, Veyras, both of (CH)

(73) Assignee: Lonza AG (CH)

( * ) Notice: Subject to any disclaimer, the term of this patent is extended or adjusted under 35 U.S.C. 154(b) by 0 days.

(21) Appl. No.: 09/670,880

(22) Filed: Sep. 27, 2000

Related U.S. Application Data

(63) Continuation of application No. PCT/EP99/04901, filed on Jul. 13, 1999.
(60) Provisional application No. 60/158,379, filed on Oct. 12, 1999.

(30) Foreign Application Priority Data

Jul. 21, 1998 (EP) .............................. 98113540

(51) Int. Cl.$^7$ ........................................... C07C 209/16
(52) U.S. Cl. ...................................... 564/479; 564/480
(58) Field of Search ..................... 564/479, 480

(56) References Cited

U.S. PATENT DOCUMENTS

| 3,331,877 A | * | 7/1967 | Smolin ....................... 564/480 |
| 4,014,933 A | * | 3/1977 | Boettger et al. ............. 564/447 |
| 4,123,462 A | * | 10/1978 | Best ............................. 564/480 |
| 4,158,017 A | * | 6/1979 | Merger et al. ............... 564/480 |
| 5,099,070 A | * | 3/1992 | Luce et al. .................. 564/480 |
| 5,288,911 A | * | 2/1994 | Koppenhoefer et al. .... 564/480 |

FOREIGN PATENT DOCUMENTS

EP     0 839 796 A2   *   5/1998   ......... C07C/209/16

OTHER PUBLICATIONS

E.B. Fleischer et al., J. Org. Chem., 1971, 36, pp. 3042–3044.*

* cited by examiner

Primary Examiner—Brian J. Davis
(74) Attorney, Agent, or Firm—Fisher, Christen & Sabol

(57) ABSTRACT

A single-stage process is described for the preparation of primary aliphatic polyamines of the formula

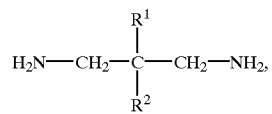

in which $R^1$ and $R^2$ independently of one another are hydrogen, methyl, ethyl or aminomethyl, by reaction of polyalcohols on a Co/Ni catalyst with supercritical ammonia in the presence of hydrogen.

16 Claims, No Drawings

PROCESS FOR THE PREPARATION OF AMINES

This application has benefit of continuation of PCT/EP99/04901 filed on Jul. 13, 1999 and U.S. Provisional Application Ser. No. 60/158,379, filed on Oct. 12, 1999.

The present invention relates to a process for the preparation of primary aliphatic polyamines from the corresponding aminoalcohols and/or polyalcohols. The polyamines which can be prepared according to the invention have the general formula

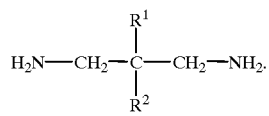

I

In this formula, $R^1$ and $R^2$ independently of one another are hydrogen, methyl, ethyl or aminomethyl.

It is, known that some primary diamines can be prepared from the corresponding alcohols or aminoalcohols. The industrially most important process of this type is the preparation of 1,2-ethanediamine (ethylenediamine) from ethanolamine. However, there are only a few processes for the analogous preparation of aliphatic polyamines of the formula I, whose efficiency is moreover low. Thus, instead, starting compounds which are complicated to prepare or complex preparation processes are chosen and usually only low yields are obtained.

U.S. Pat. No. 4,123,462 discloses a method for the preparation of amines using a nickel/rhenium catalyst. The examples given indicate the amination of 1,3-propanediol with a conversion of 45%. Details of the product yields or selectivities are not mentioned.

In U.S. Pat. No. 4,158,017, hydroxypivalaldehyde is employed as a starting compound in order to obtain the corresponding diamine (2,2-dimethyl-1,3-propane-diamine, "neopentyldiamine"). Hydroxypivalaldehyde is a starting compound which is complicated to prepare, whose amination needs a number of reaction stages. Because of this, this process is not very economical.

According to U.S. Pat. No. 5,099,070, it is essential for the preparation of neopentyldiamine by reaction of neopentanolamine (3-amino-2,2-dimethyl-1-propanol) with ammonia in the presence of hydrogen on a nickel catalyst that the starting material is free of neopentyl glycol in order to avoid, possible side reactions of the diol such as hydrogenolysis.

In U.S. Pat. No. 5,288,911, a catalyst of cobalt and iron is used in order preferably to produce (x,(i)-aminoalcohols from (x,(i)-alkanediols. From the examples disclosed, it is evident that the diamine is only obtained as a byproduct. The process shown is (therefore not suitable for the industrial preparation of the diamine.

The prior art does not disclose any process by means of which primary aliphatic polyamines having more than two terminal amino groups can be obtained directly from the corresponding alcohol of the formula I. The industrial preparation of compounds of this product class, e.g. 2-aminomethyl-2-methyl-1,3-propanediamine ("1,1,1-tris(aminomethyl)ethane"), 2-aminomethyl-2-ethyl-1,3-propanediamine ("1,1,1-tris(aminomethyl) propane") or 2,2-bis(aminomethyl)-1,3-propanediamine ("pentaerythrityltetramine") from the corresponding easily accessible polyalcohols, however, is particularly attractive. A known multi-stage synthesis (E. B. Fleischer et al., *J. Org. Chem.* 1971, 36, 3042) requires the azide as an intermediate. Azides are prone to explosive decomposition, which does not make them very suitable for industrial processes.

The object of the present invention was therefore to make available a process suited to being carried out on an industrial scale, which in one stage yields primary aliphatic polyamines from the corresponding polyols.

According to the invention, this object is achieved by the process according to Patent claim 1.

Starting from primary aliphatic polyalcohols of the general formula

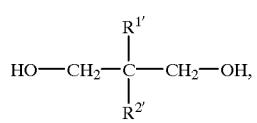

II in which $R^{1'}$ has the meaning mentioned above for $R^1$ or, if $R^1$ is aminomethyl, $R^{1'}$ can also be hydroxymethyl, and $R^{2'}$ has the meaning mentioned above for $R^2$ or, if $R^2$ is aminomethyl, $R^{2'}$ can also be hydroxymethyl, it was found that by reaction with ammonia in the presence of hydrogen the corresponding primary polyamines can be obtained in single-stage process if a catalyst containing nickel and/or cobalt is employed and the ammonia is in the supercritical state, i.e. under a pressure of more than 113 bar and at a temperature of more than 133° C., and the quantitative ratio is 1–300 mol of ammonia and 0.01–20 mol of hydrogen to 1 equivalent (eq.) of polyalcohol II.

The pressure is preferably 115–300 bar and the temperature 150–300° C.

Pressures of 120–200 bar and temperatures of 160–250° C. are particularly preferred.

The quantitative ratio is preferably 10–100 mol, particularly preferably 40–90 mol, of ammonia and 2–10 mol, of hydrogen to 1 equivalent (eq.)of polyalcohol.

The metal fraction of the catalyst preferably has a content of 5–95 percent by weight nickel and/or cobalt.

Catalysts are particularly preferred which additionally contain 1–60 percent by weight of Fe and/or La as a further metal.

It has moreover been shown that the catalyst should not be too basic or too acidic.

The catalysts employable according to the invention can be prepared, for example, by precipitating the hydroxides, hydrated oxides and/or hydroxycarbonates of the active metals at a pH of 5–9, and drying and calcining them at 200–500° C. in an oxidizing atmosphere.

A certain number and concentration of basic and acidic centres on the catalyst surface are advantageous for the amination of the alcohols, as the adsorption and activation of ammonia and of the aminoalcohol, which recurs as an intermediate require these centres. Strongly basic and strongly acidic centres on the catalyst surface, however, should be avoided. Such centres are induced, for example, by reagents having strongly basic ions such as, for example, sodium, potassium, calcium, barium or strongly acidic ions such as, for example, phosphate, hydrogenphosphate. In this context, the basicity or acidity relates to the action on the solids surface and not to the customarily considered properties in solution. It was found that centres of this type have an adverse effect on the selectivity of the reaction to give the desired products, and base- or acid-catalysed side reactions such as fragmentation, cyclization and oligomerization are favoured. One possibility of influencing the acidic and basic properties of the catalyst is the checking of the pH during the precipitation of the catalyst. The precipitation should therefore be carried out at a pH of 5–9. Furthermore, it is advantageous to wash the precipitate carefully.

The precipitation can be carried out, for example, by addition of a base to a solution of the acetates, nitrates or halides of the metal component(s). Preferred bases for this are ammonium carbonate and carbamate or ammonia. Drying is preferably carried out at temperatures tip to 150° C., if appropriate in vacuo.

The catalyst is preferably calcined at 300–500° C. in an oxidizing atmosphere.

For the catalyst, a support such as silica, kieselguhr, alumina or graphite can be used. For this purpose, the precipitation can be carried out in the presence of the support.

Before use, the catalyst is advantageously activated at temperatures of 200 to 400° C. by reducing gases such as, for example, hydrogen.

The process according to the invention can be carried out with unbranched and branched polyalcohols II. 1,3-Propanediol 2-methyl-1,3-propanediol, 2,2'-dimethyl-1,3-propanediol, 1,1,1-tris(hydroxymethyl)-ethane and pentaerythritol are particularly preferred.

The process according to the invention can be carried out batchwise or continuously; the continuous procedure is preferred.

The contact time (defined as the quotient of catalyst mass [g] and supplied molar flow [mol/s] of the reaction components) when carrying out the process continuously is preferably 10,000 g·s/mol. to 100,000 g·s/mol.

In the continuous procedure, the unreacted polyalcohol and/or the unreacted ammonia is preferably recycled. By this means, even with (after a single passage) a relatively low conversion a satisfactory to good product yield can be achieved.

The ammonia can be supplied to the reaction vessel as a gas, but preferably as a liquid; the supercritical state can then be achieved starting from the gas or the liquid phase. In the case of solid starting materials, the use of liquid ammonia has the advantage that these can already be dissolved before achieving the supercritical state and the reaction mixture is thus present from the start as a homogeneous phase. The reaction mixture is advantageously cooled after the reaction, e.g. by adiabatic expansion, and the ammonia is separated off and optionally fed back into the process.

The aliphatic primary polyamines of the formula I which can be prepared by the process according to the invention can be employed, for example, for polyurethane preparation, in particular as crosslinkers and/or catalysts having a low migration tendency.

The following examples explain how the process according to the invention is carried out.

EXAMPLE 1

Preparation of a Co/Fe Catalyst

The salts $Co(NO_3)_2 \cdot 6 H_2O$ and $Fe(NO_3)_3 \cdot 9 H_2O$ were dissolved in water in a molar ratio of 20:1 and a total concentration of 0.36 mol/l and treated at pH 7 with 100 g of a 20% strength aqueous solution of commercial "ammonium carbonate" (mixture of carbamate and carbonate), cobalt and iron precipitating as hydroxycarbonates. The precipitate was filtered off, washed carefully with water, dried at 100° C. and calcined at 400° C. Before use, the catalyst thus obtained was activated with hydrogen at 330° C.

EXAMPLE 2

Preparation of 1,3-propanediamine

The reaction was carried out in a batchwise reactor system. The reactor consisted of an Inconel® 718 tube having an internal diameter of 13 mm and a length of 304 mm. It contained 8 g of the Co/Fe catalyst from the above example. A reaction mixture of 1,3-propanediol ammonia and hydrogen in the molar ratio 1:60:2 was pumped through the reactor from the top downwards and converted to 35% at a temperature of 160° C., a pressure of 135 bar and with a contact time (for definition see above) of 40,000 g·s/mol. The product contained 1,3-diaminopropane with a selectivity of 33% and 3-amino-1-propanol with a selectivity of 67%.

EXAMPLE 3

Preparation of 1,3-propanediamine

The procedure was as described in Example 2, but the reaction temperature was 195° C. and the contact time 60,000 g·s/mol, the conversion was 95%, the yield of 1,3-propanediamine 32%. 8% of 3-amino-1-propanol and 40% of other products were furthermore found.

EXAMPLE 4

Comparison Example

The reactor system from Example 2 was charged with 8 g of a commercial supported nickel catalyst (Engelhard Ni-6458). The metal content of this catalyst is 56%; the support consists of silica. This catalyst has only a low acidic character, which it was possible to determine by ammonia adsorption measurements. A reaction mixture of 2,2-dimethyl-1,3-propanediol, ammonia and hydrogen in the molar ratio 1:60:2 was converted to 84% at a temperature of 210° C., a pressure of 135 bar and with a contact time of 40,000 g·s/mol. 1,3-Diamino-2,2-dimethylpropane was obtained with a selectivity of 70%, 3-amino-2,2-dimethyl-1-propanol resulted as a by product or intermediate with a selectivity of 10%. The Comparison Example was carried out under the same reaction conditions, apart from the fact that the pressure of 135 bar was lowered below the critical pressure of ammonia (113 bar) to 90 bar. Table 1 shows the results obtained.

TABLE 1

| Example | Pressure [bar] | Conversion [%] | Di-amine | Aminol | Fragments*[1] | Other |
|---|---|---|---|---|---|---|
| 4 | 135 | 75 | 70 | 10 | 9 | 11 |
| Comparison | 90 | 69 | 18 | 3 | 20 | 59 |

*[1]in the liquid product

Selectivity [%]

Table 1 explains the significant influence of the supercritical state on the selectivity of the amination. If the pressure falls from 135 bar to 90 bar, the selectivity of the diamine formation falls from 70% to 18%, while the formation of by-products greatly increases.

EXAMPLE 5

Analogously to Example 4, a reaction mixture of 1,1,1-tris(hydroxymethyl)ethane, ammonia and hydrogen was reacted in a molar ratio of 1:90:3 at a temperature of 195° C., a pressure or 135 bar and with a contact time of 40,000 g·s/mol. The conversion was 97%, the yield of 1,1,1-tris(aminomethyl)ethane 13%.

EXAMPLE 6

The reactor system from Example 2 was provided with 8 g of a commercial cobalt supported catalyst (Engelhard Co-0138). The metal content of this catalyst is 25%; the support consists of silica. A reaction mixture consisting of 1,1,1-tris (hydroxymethyl) ethane, ammonia and hydrogen in the molar ratio 1:90:3 was reacted at a temperature of 185° C., a pressure of 135 bar and with a contact time of 30,000 g·s/mol. The conversion was 97%, the yield of 1,1,1-tris(aminoethyl)ethane 10%.

What is claimed, is:

1. A process for the preparation of primary aliphatic polyamines of the general formula

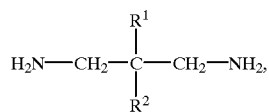

I in which $R^1$ and $R^2$ independently of one another are hydrogen, methyl ethyl or aminomethyl, by reaction of the corresponding polyalcohols of the general formula

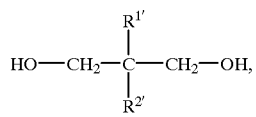

II in which
$R^{1'}=R^1$ or, if $R^1$ is aminomethyl, $R^{1'}$ can also be hydroxymethyl, and $R^{2'}=R^2$ or if $R^2$ is aminomethyl, $R^{2'}$ can also be hydroxymethyl,
with ammonia in the presence of hydrogen, characterized in that the reaction is carried out with supercritical ammonia in the presence of a catalyst containing Ni and/or Co at a ratio of 1 to 300 mol of ammonia and 0.01 to 20 mol of hydrogen to 1 eq. of alcohol.

2. The process according to claim 1, characterized in that the metal fraction of the catalyst contains 5 to 95% by weight of Ni and/or Co.

3. The process according to claim 2, characterized in that the catalyst additionally contains 1 to 60% by weight of Fe and/or La.

4. The process according to claim 3, characterized in that the catalyst is prepared by precipitation of the corresponding hydroxides, hydrated oxides and/or basic carbonates at a pH of 5 to 9 and subsequent drying and calcination at 2000 to 500° C. in an oxidizing atmosphere.

5. The process according to claim 4, characterized in that the catalyst is applied to a support of silica kieselguhr, alumina or graphite.

6. The process according to claim 5, characterized in that the catalyst is activated with hydrogen at a temperature of 200 to 400° C.

7. The process according to claim 6, characterized in that the aliphatic polyalcohol II is selected from the group consisting of 1,3-propanediol, 2-methyl-1,3-propanediol, 2,2'-dimethyl-1,3-propanediol, 1,1,1-tris(hydroxymethyl) ethane and pentaerythritol.

8. The process according to claim 7, characterized in that the process is carried out continuously.

9. The process according to claim 8, characterized in that the contact time is 10,000 to 100,000 g·s/mol.

10. The process according to claim 9, characterized in that the unreacted polyalcohol II and/or the unreacted ammonia is recycled.

11. The process according to claim 1, characterized in that the catalyst is prepared by precipitation of the corresponding hydroxides, hydrated oxides and/or basic carbonates at a pH of 5 to 9 and subsequent drying and calcination at 2000 to 500° C. in an oxidizing atmosphere.

12. The process according to claim 1, characterized in that the catalyst is applied to a support of silica, kieselguhr, alumina or graphite.

13. The process according to claim 1, characterized in that the catalyst is activated with hydrogen at a temperature of 200° to 400° C.

14. The process according to claim 1, characterized in that the aliphatic polyalcohol II is selected from the group consisting of 1,3-propanediol, 2-methyl-1,3-propanediol, 2,2'-dimethyl-1,3-propanediol, 1,1,1-tris(hydroxymethyl) ethane and pentaerythritol.

15. The process according to claim 1, characterized in that the process is carried out continuously.

16. The process according to claim 8, characterized in that the unreacted polyalcohol II and/or the unreacted ammonia is recycled.

* * * * *